United States Patent [19]

Stroech et al.

[11] Patent Number: 5,162,355
[45] Date of Patent: Nov. 10, 1992

[54] FUNGICIDAL 1,2,4-TRIAZOLYL-PROPANOLS

[75] Inventors: Klaus Stroech, Solingen; Manfred Jautelat, Burscheid; Heinz-Wilhelm Dehne, Ahnsen; Stefan Dutzmann, Hilden; Gerd Hänssler, Leverkusen, all of Fed. Rep. of Germany

[73] Assignee: Bayer Aktiengesellschaft, Leverkusen, Fed. Rep. of Germany

[21] Appl. No.: 658,938

[22] Filed: Feb. 21, 1991

[30] Foreign Application Priority Data

Feb. 28, 1990 [DE] Fed. Rep. of Germany ....... 4006223

[51] Int. Cl.$^5$ ................ A01N 43/653; C07D 249/08
[52] U.S. Cl. ................... 514/383; 548/267.8
[58] Field of Search ............ 548/101, 267.8; 514/184, 383

[56] References Cited

U.S. PATENT DOCUMENTS 4,551,469 11/1985 Parry et al. ............... 514/383
4,913,727 4/1990 Stroech et al. ............ 71/92
4,923,502 5/1990 Elliott et al. ............. 548/267.8

*Primary Examiner*—Patricia L. Morris

*Attorney, Agent, or Firm*—Sprung Horn Kramer & Woods

[57] ABSTRACT

Fungicidal 1,2,4-triazolyl-propanols of the formula

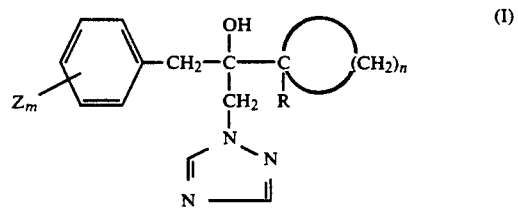

in which

R represents methyl or ethyl,

Z represents fluorine, chlorine, trifluoromethyl, trifluoromethoxy, trifluoromethylthio, methyl, phenyl which is optionally substituted by fluorine or chlorine or phenoxy which is optionally substituted by fluorine or chlorine, m represents 0, 1, 2 or 3 and n represents 4 or 5, and addition products thereof with acids and metal salts.

3 Claims, No Drawings

FUNGICIDAL 1,2,4-TRIAZOLYL-PROPANOLS

The present application relates to new 1,2,4-triazolyl-propanol derivatives, to several processes for their preparation and to their use as fungicides.

It has already been disclosed that numerous azolyl-methyl-cyclopropyl derivatives have fungicidal properties (compare EP-OS (European Published Specification) 0,297,345). Thus, for example, 1-(4-chlorophenyl)-2-(1-methyl-cycloprop-1-yl)-3-(1,2,4-triazol-1-yl)-propan-2-ol can be employed for combating fungi. The activity of this substance is good; however, in some cases it leaves something to be desired at low application rates.

It is furthermore known that certain hydroxyethyl-azolyl derivatives substituted by cycloalkyl have fungicidal properties (compare U.S. Pat. No. 4,551,469). However, the activity of these substances is also not always completely sufficient.

New 1,2,4-triazolyl-propanol derivatives of the formula

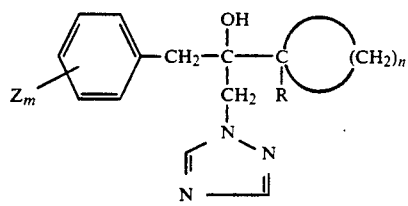 (I)

in which
R represents methyl or ethyl,
Z represents fluorine, chlorine, trifluoromethyl, trifluoromethoxy, trifluoromethylthio, methyl, phenyl which is optionally substituted by fluorine or chlorine or phenoxy which is optionally substituted by fluorine or chlorine,
m represents 0, 1, 2 or 3 and
n represents 4 or 5,
and their acid addition salts and metal salt complexes have now been found.

It has furthermore been found that 1,2,4-triazolyl-propanol derivatives of the formula (I) and their acid addition salts and metal salt complexes are obtained when a) propanol derivatives of the formula

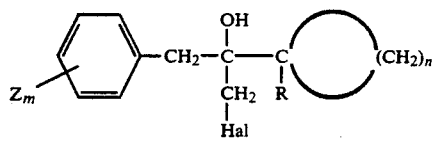 (II)

in which
R, Z, m and n have the abovementioned meanings, and
Hal represents chlorine, bromine or iodine,
are reacted with 1,2,4-triazole of the formula

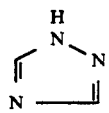 (III)

in the presence of an acid-binding agent and in the presence of a diluent, or b) oxiranes of the formula

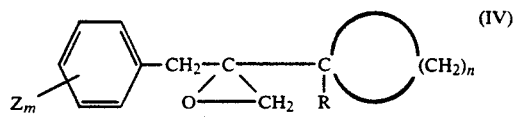 (IV)

in which
R, Z, m and n have the abovementioned meanings,
are reacted with 1,2,4-triazole of the formula

 (III)

in the presence of an acid-binding agent and in the presence of a diluent,
or c) triazolylmethyl ketones of the formula

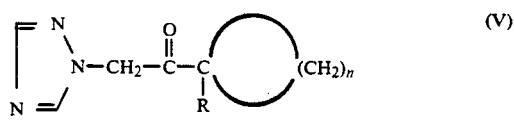 (V)

in which R and n have the abovementioned meanings,
are reacted with organometallic compounds of the formula

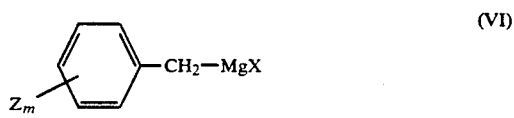 (VI)

in which
Z and m have the abovementioned meanings and
X represents chlorine, bromine or iodine,
in the presence of a diluent,
and, if desired, an acid or a metal salt is subsequently adducted to the compounds of the formula (I) thus obtained.

Finally, it has been found that the new 1,2,4-triazolyl-propanol derivatives of the formula (I) and their acid addition salts and metal salt complexes have strong fungicidal properties.

The substances according to the invention contain an asymmetrically substituted carbon atom. They can therefore occur in optical isomeric forms. The present invention relates both to the individual isomers and to their mixtures.

Surprisingly, the substances according to the invention have better fungicidal properties than the previously known compounds which are most similar in terms of constitution, of the same line of action.

If m in the formula (I) represents the numbers 2 or 3, the Z radicals can be identical or different.

The acids which can be adducted to the 1,2,4-triazolyl-propanol derivatives of the formula (I) preferably include hydrohalic acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid, and additionally also saccharin.

The metal salts which can be adducted to the 1,2,4-triazolyl-propanol derivatives of the formula (I) preferably include salts of metals of main groups II to IV and sub-groups I and II and IV to VIII of the Periodic Table of the Elements.

In this connection, salts of copper, zinc, manganese, magnesium, tin, iron and nickel are particularly preferred. Suitable anions of these salts are those which are derived from those acids which lead to physiologically tolerable addition products.

Particularly preferred acids of this type in this connection are the hydrohalic acids, such as, for example, hydrochloric acid and hydrobromic acid, and furthermore phosphoric acid, nitric acid and sulphuric acid.

The substances shown in the following table may be mentioned as examples 1,2,4-triazolyl-propanol derivatives of the formula (I).

TABLE 1

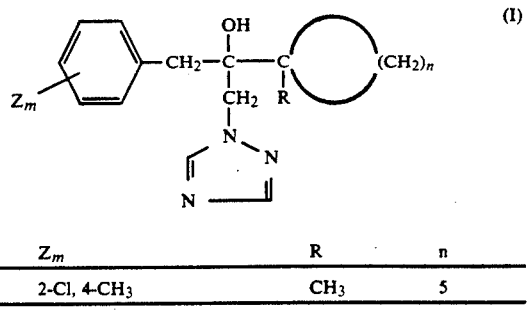

| $Z_m$ | R | n |
|---|---|---|
| 2-Cl | $C_2H_5$ | 4 |
| 4-Cl | $C_2H_5$ | 5 |
| 4-$CF_3$ | $CH_3$ | 4 |
| 4-$CF_3O$ | $CH_3$ | 5 |
| 4-$CF_3S$ | $CH_3$ | 5 |
| 4-(phenyl) | $CH_3$ | 5 |
| 4-(4-chlorophenyl) | $CH_3$ | 5 |
| 4-O-(phenyl) | $CH_3$ | 5 |
| 4-O-(4-chlorophenyl) | $CH_3$ | 5 |
| — | $CH_3$ | 5 |
| — | $C_2H_5$ | 5 |
| 2,4-$Cl_2$ | $C_2H_5$ | 4 |
| 2,4,6-$Cl_3$ | $CH_3$ | 5 |
| 2-$CH_3$ | $CH_3$ | 4 |
| 4-$CH_3$ | $CH_3$ | 5 |
| 2,4-$F_2$ | $CH_3$ | 5 |
| 2-Cl, 4-$CH_3$ | $CH_3$ | 4 |

TABLE 1-continued

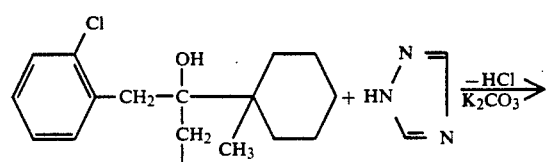

| $Z_m$ | R | n |
|---|---|---|
| 2-Cl, 4-$CH_3$ | $CH_3$ | 5 |

If 1-chloro-3-(2-chlorophenyl)-2-(1-methylcyclohex-1-yl)-propan-2-ol and 1,2,4-triazole are used as starting materials, the course of process (a) according to the invention can be illustrated by the following equation:

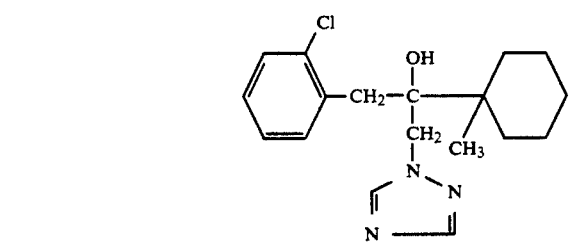

If 2-[(2-chlorophenyl)-methyl]-2-(1-methylcyclopent-1-yl)-oxirane and 1,2,4-triazole are used as starting materials, the course of process (b) according to the invention can be illustrated by the following equation:

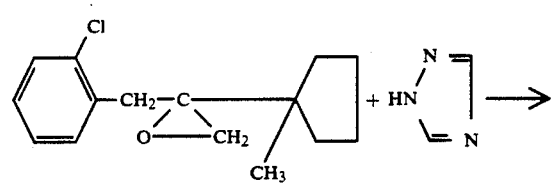

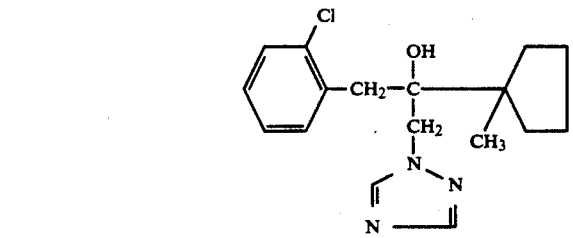

If 1,2,4-triazol-1-yl-methyl 1-methylcyclohex-1-yl ketone and 4-fluoro-benzyl-magnesium bromide are used as starting materials, the course of process (c) according to the invention can be illustrated by the following equation:

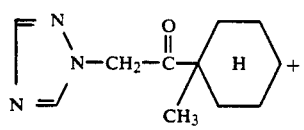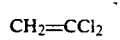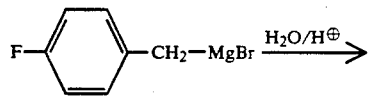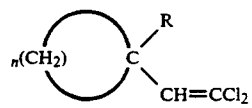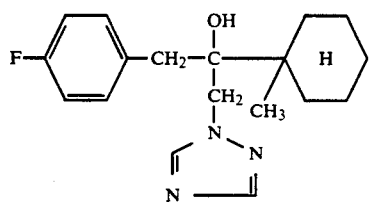

Formula (II) provides a definition of the propanol derivatives required as starting materials in process (a) according to the invention. In this formula, R, Z, m and n preferably have those meanings which have already been mentioned for these radicals or these indices in connection with the description of the substances of the formula (I) according to the invention. Hal preferably represents chlorine or bromine.

The propanol derivatives of the formula (II) were not known until now. They can be prepared by a process in which cyloalkyl ketones of the formula

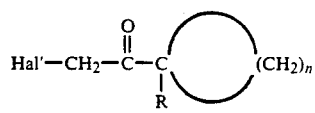

(VII)

in which
R and n have the abovementioned meanings and
Hal' represents chlorine or bromine,
are reacted with organometallic compounds of the formula

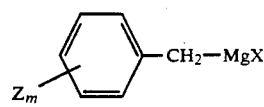

(VI)

in which
X, Z and m have the abovementioned meanings, in the presence of a diluent.

The cycloalkyl ketones of the formula (VII) required as starting materials for the preparation of the propanol derivatives by the above process are known in some cases (compare EP-OS (European Published Specification) 0,055,427). They can be prepared by a process in which cycloalkyl compounds of the formula

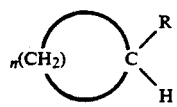

(VIII)

in which
R and n have the abovementioned meanings,
are reacted with 1,1-dichloroethene of the formula $CH_2=CCl_2$     (IX)

in the presence of tert.-butyl chloride and aluminum chloride at temperatures between $-20°$ C. and $+10°$ C. and the 2,2-dichloroethenyl-cycloalkyl derivatives formed in this way of the formula

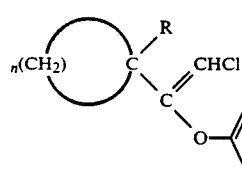

(X)

in which
R and n have the abovementioned meanings,
are reacted with sodium phenoxide in the presence of an acid-binding agent, such as, for example, potassium carbonate, and in the presence of a diluent, such as, for example, N-methylpyrrolidone, at temperatures between $50°$ C. and $220°$ C. and the substances formed in this way of the formula

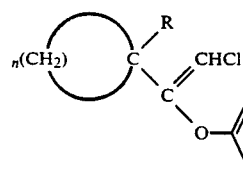

(XI)

in which
R and n have the abovementioned meanings,
are reacted with acids, such as, for example, formic acid, if appropriate in the presence of a diluent, such as, for example, methanol or ethanol, and in the presence of water.

The organometallic compounds of the formula (VI) required as reaction components in the above process for the preparation of propanol derivatives of the formula (II) are known or can be synthesized by methods which are known in principle. Thus, compounds of the formula (VI) are obtained by a process in which benzyl halides of the formula

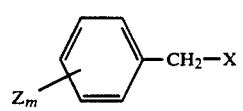

(XII)

in which
X, Z and m have the abovementioned meanings,
are reacted with magnesium in the presence of an inert diluent, such as, for example, diethyl ether, at temperatures between $0°$ C. and $50°$ C.

The benzyl halides of the formula (XII) are generally known compounds of organic chemistry.

Suitable diluents for the above process for the preparation of propanol derivatives of the formula (II) are all inert organic solvents customary for reactions of this type. Those which can preferably be used are ethers, such as diethyl ether, tetrahydrofuran and dioxane.

The reaction temperatures can be varied within a certain range when carrying out the above process for the preparation of propanol derivatives of the formula (II). In general, the reaction is carried out at temperatures between $-80°$ C. and $+100°$ C., preferably between $-80°$ C. and $+60°$ C.

When carrying out the above process for the preparation of propanol derivatives of the formula (II), the reaction is in general carried out at normal pressure. However, it is also possible to work at elevated or reduced pressure.

When carrying out the above process for the preparation of propanol derivatives of the formula (II), 1 to 1.2 mols of organometallic compound of the formula (VI), which is expediently prepared immediately beforehand and further processed in situ, are in general employed relative to 1 mol of cycloalkyl ketone of the formula (VII). Working-up is carried out by customary methods. In general, a procedure is used in which the mixture is first acidified and water is added, then the organic phase is separated off, washed and concentrated after drying.

Possible acid-binding agents for carrying out process (a) according to the invention are all customary inorganic and organic bases. Those which can preferably be used are alkali metal carbonates, such as sodium carbonate and potassium carbonate, additionally alkali metal hydroxides, such as sodium hydroxide and potassium hydroxide, moreover alkali metal alkoxides, such as sodium methoxide and potassium methoxide and sodium ethoxide and potassium ethoxide and also potassium tert.-butoxide, and furthermore lower tertiary alkylamines, cycloalkylamines and aralkylamines, such as, in particular, triethylamine.

Suitable diluents for carrying out process (a) according to the invention are all customary inert organic solvents. Those which can preferably be used are nitriles, such as acetonitrile, additionally aromatic hydrocarbons, such as benzene, toluene and dichlorobenzene, moreover formamides, such as dimethylformamide, and also strongly polar solvents, such as dimethyl sulphoxide and hexamethylphosphoramide.

The reaction temperatures can be varied within a relatively wide range when carrying out process (a) according to the invention. In general, the reaction is carried out at temperatures between 0° C. and 200° C., preferably between 60° C. and 150° C.

Process (a) according to the invention, like processes (b) and (c) according to the invention, is generally carried out at normal pressure. However, it is also possible in each case to work at elevated or reduced pressure.

When carrying out process (a) according to the invention, 1 to 4 mols of 1,2,4-triazole of the formula (III) and 1 to 3 mols of acid-binding agent are in general employed relative to 1 mol of propanol derivative of the formula (II). In some cases it is expedient to work under a protective gas atmosphere. Working-up is carried out by customary methods. In general, a procedure is used in which the reaction mixture is concentrated by stripping off the diluent, the residue which remains is taken up in a virtually water-immiscible organic solvent, and the organic phase is washed and, after drying, concentrated. The product which remains may optionally be subjected to further purification processes.

The oxiranes of the formula (IV) required as starting materials for process (b) according to the invention were not known until now. They can be prepared by a process in which propanol derivatives of the formula

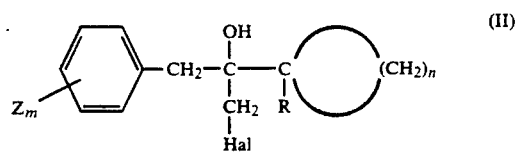

in which
R, Z, Hal, m and n have the abovementioned meanings,
are reacted with bases in the presence of a diluent.

Suitable bases for the preparation of oxiranes of the formula (IV) by the above process are all inorganic and organic bases customarily suitable for reactions of this type. Those which can preferably be used are all bases of the type which have already been mentioned as preferred acid-binding agents in connection with the description of process (a) according to the invention.

The reaction temperatures can be varied within a certain range in the preparation of oxiranes by the above process. In general, the reaction is carried out at temperatures between −30° C. and +100° C., preferably between −20° C. and +60° C.

When carrying out the above process for the preparation of oxiranes of the formula (IV), the reaction is in general carried out at normal pressure. However, it is also possible to work at elevated or reduced pressure.

When carrying out the above process for the preparation of oxiranes of the formula (IV), 1 to 3 mols of base are in general employed relative to 1 mol of propanol derivative of the formula (II). Working-up is carried out by customary methods.

Possible acid-binding agents and diluents for carrying out process (b) according to the invention are all acid-binding agents and diluents which can customarily be employed for reactions of this type. Those which can preferably be used are all acid-binding agents and diluents of the type which have already been mentioned as preferred acid-binding agents and diluents in connection with the description of process (a) according to the invention.

The reaction temperatures can be varied within a relatively wide range when carrying out process (b) according to the invention. In general, the reaction is carried out at temperatures between 0° C. and 200° C., preferably between 60° C. and 150° C.

When carrying out process (b) according to the invention, 1 to 2 mols of 1,2,4-triazole of the formula (III) and 1 to 2 mols of acid-binding agent are in general employed relative to 1 mol of oxirane of the formula (IV). Working-up is carried out by customary methods.

The triazolylmethyl ketones of the formula (V) required as starting materials in process (c) according to the invention are known in some cases. They can be prepared by a process in which cycloalkyl ketones of the formula

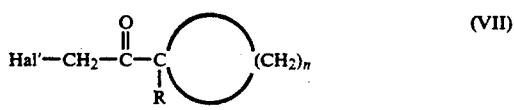

in which
R, Hal, and n have the abovementioned meanings,
are reacted with 1,2,4-triazole of the formula

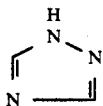 (III)

in the presence of an acid-binding agent and, if appropriate, in the presence of a diluent.

Possible acid-binding agents and diluents for the preparation of triazolylmethyl ketones of the formula (V) by the above process are all acid-binding agents and diluents which can customarily be used for reactions of this type. Those which can preferably be used are all acid-binding agents of the type which have already been mentioned as preferred acid-binding agents in connection with the description of process (a) according to the invention. Suitable diluents are preferably ketones, such as acetone, and nitriles, such as acetonitrile.

The reaction temperatures can be varied within a relatively wide range in the preparation of triazolylmethyl ketones of the formula (V) by the above process. In general, the reaction is carried out at temperatures between 0° C. and 120° C., preferably between 20° C. and 100° C.

The above process for the preparation of triazolylmethyl ketones of the formula (V) is in general carried out at normal pressure.

When carrying out the above process for the preparation of triazolylmethyl ketones of the formula (V), 1 to 4 mols of 1,2,4-triazole of the formula (III) and 1 to 3 mols of acid-binding agent are in general employed relative to 1 mol of cycloalkyl ketone of the formula (VII). Working-up is carried out by customary methods.

The organometallic compounds of the formula (VI) required as reaction components for process (c) according to the invention have already been mentioned in connection with the description of the process for the preparation of the propanol derivatives of the formula (II).

When carrying out process (c) according to the invention, suitable diluents are all customary inert organic solvents. Those which can preferably be used are ethers, such as diethyl ether, tetrahydrofuran and dioxane.

The reaction temperatures can be varied within a relatively wide range when carrying out process (c) according to the invention. In general, the reaction is carried out at temperatures between −80° C. and +60° C., preferably between −70° C. and +50° C.

When carrying out process (c) according to the invention, 0.8 to 2 mols of organometallic compound of the formula (VI), which has expediently been prepared immediately beforehand and further processed in situ, are in general employed relative to 1 mol of triazolylmethyl ketone of the formula (V). Working-up is carried out by customary methods.

The 1,2,4-triazolyl-propanol derivatives of the formula (I) obtainable by the process according to the invention can be converted into acid addition salts or metal salt complexes.

In order to prepare acid addition salts of the compounds of the formula (I), possible acids are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and are isolated in a known manner, for example by filtering off, and, if desired, are purified by washing with an inert organic solvent.

In order to prepare metal salt complexes of the compounds of the formula (I), suitable metal salts are preferably those which have already been mentioned as preferred metal salts in connection with the description of the metal salt complexes according to the invention.

The metal salt complexes of the compounds of the formula (I) can be obtained in a simple manner by customary methods, thus, for example by dissolving the metal salt in alcohol, for example ethanol, and adding to compounds of the formula (I). Metal salt complexes can be isolated in a known manner, for example by filtering off, and, if desired, purified by recrystallization.

The active compounds according to the invention have a strong microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubense;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea;*
(conidia form: Drechslera, syn: Helminthosporium);
Cochliobolus species, such as *Cochliobolus sativus;*
(conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae* and
Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal and rice diseases, such as Pseudocercosporella herpotrichoides, Septoria nodorum, Cochliobolus sativus, Pyrenophora teres, Fusarium spp., Erysiphe, Pyricularia and Pellicularia. They can used to particularly good effect against Pyricularia oryzae and Pellicularia sasakii on rice. They are furthermore suitable for combating Venturia and Botrytis in fruit, vine and vegetable cultivation. Moreover, the substances according to the invention also show a good in vitro action.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

When using the substances according to the invention as fungicides, the amount applied can be varied within a relatively wide range depending on the type of application. Thus, in the treatment of parts of plants, the active compound concentrations in the use forms are, in general, between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02%, are required at the place of action.

The preparation and use of the active compounds according to the invention can be seen from the following examples.

PREPARATION EXAMPLES

Example 1

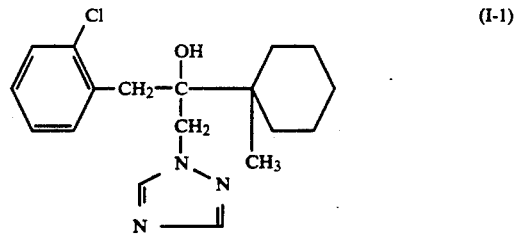

(I-1)

12 g (174 mmol) of 1,2,4-triazole and 17 g (123 mmol) of potassium carbonate are initially introduced into 30 ml of absolute dimethylformamide under a nitrogen atmosphere and the mixture is heated to 80° C. At this temperature, a solution of 16.7 g (55.5 mmol) of 1-chloro-3-(2-chlorophenyl)-2-(1-methyl-cyclohex-1-yl)-propan-2-ol in 20 ml of absolute dimethylformamide is added dropwise with stirring. The reaction mixture is then stirred at 80° C. for a further 8 hours. The precipitate is filtered off with suction, and the filtrate is concentrated by stripping off the diluent under reduced pressure. The residue is taken up in ethyl acetate, washed with water and, after drying over sodium sulphate, the solvent is stripped off under reduced pressure. The product which remains is chromatographed through a silica gel column using dichloromethane/ethanol=99:1 as the eluent. 8.6 g (46.5% of theory) of 1-(2-chlorophenyl)-2-(1-methyl-cyclohex-1-yl)-3-(1,2,4-triazol-1-yl)-propan-2-ol are obtained in this manner in the form of a solid substance of melting point 105° C.
Preparation of the precursor of the formula

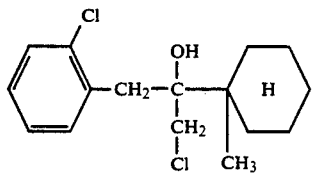
(II-1)

A solution of 10.1 g (63 mmol) of 2-chloro-benzyl chloride in 30 ml of absolute diethyl ether is added dropwise under a nitrogen atmosphere to a mixture of 1.6 g (66 mmol) of magnesium turnings and a crystal of iodine in 10 ml of absolute diethyl ether in such a way that the diethyl ether gently boils. The mixture is stirred at boiling point for 30 minutes and then cooled to room temperature, and the Grignard solution prepared in this way is added dropwise with stirring to a solution of 10 g (57 mmol) of 1-chloroacetyl-1-methyl-cyclohexane in 40 ml of absolute diethyl ether. The reaction mixture is stirred at 20° C. for 4 hours, saturated aqueous ammonium chloride solution is then added and the mixture is poured into water. It is extracted using ethyl acetate and the combined organic phases are washed with water, dried over sodium sulphate and concentrated by stripping off the solvent under reduced pressure. 16.7 g (97% of theory) of 1-chloro-3-(2-chlorophenyl)-2-(1-methylcyclohex-1-yl)-propan-2-ol remain in the form of an oil.

$^1$H-NMR (200 MHz, CDCl$_3$): δ=1.13 (s) and 1.05–1.7 (m, 13H), 1.82 (d, 1H), 2.62 (dd, 1H), 3.06 (d, 1H), 3.38 (d, 1H), 7.1–7.38 (m, 4H) ppm.

Example 2

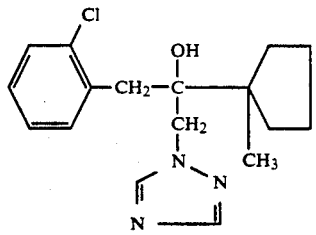
(I-2)

13 g (188 mmol) of 1,2,4-triazole and 18 g (130 mmol) of potassium carbonate are initially introduced into 30 ml of absolute dimethylformamide under a nitrogen atmosphere and the mixture is heated to 80° C. At this temperature, a solution of 17.1 g (59.6 mmol) of 1-chloro-3-(2-chlorophenyl)-2-(1-methyl-cyclopent-1-yl)-propan-2-ol in 20 ml of absolute dimethylformamide is added dropwise with stirring. The reaction mixture is then stirred at 80° C. for a further 8 hours. The precipitate is filtered off with suction, and the filtrate is concentrated by stripping off the diluent under reduced pressure. The residue is taken up in ethyl acetate, washed with water and, after drying over sodium sulphate, the solvent is stripped off under reduced pressure. The product which remains is chromatographed through a silica gel column using dichloromethane/ethanol=99:1 as the eluent. 6.8 g (35.7% of theory) of 1-(2-chlorophenyl)-2-(1-methyl-cyclopent-1-yl)-3-(1,2,4-triazol-1-yl)-propan-2-ol are obtained in this way in the form of a solid substance of melting point 110° C.
Preparation of starting materials:

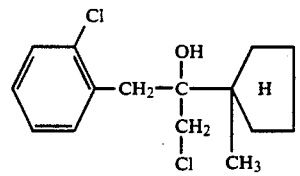
(II-2)

A solution of 11 g (68 mmol) of 2-chloro-benzyl chloride in 30 ml of absolute diethyl ether is added dropwise under a nitrogen atmosphere to a mixture of 1.7 g (70 mmol) of magnesium turnings and a crystal of iodine in 10 ml of absolute diethyl ether in such a way that the diethyl ether gently boils. The mixture is stirred at boiling point for 30 minutes and then cooled to room temperature, and the Grignard solution prepared in this way is added dropwise with stirring to a solution of 10 g (62 mmol) of 1-chloroacetyl-1-methyl-cyclopentane in 40 ml of absolute diethyl ether. The reaction mixture is stirred at 20° C. for 4 hours, saturated aqueous ammonium chloride solution is added and the mixture is poured into water. It is extracted with ethyl acetate, washed and concentrated by stripping off the solvent under reduced pressure. 17.1 g (96% of theory) of 1-chloro-3-(2-chlorophenyl)-2-(1-methyl-cyclopent-1-yl)-propan-2-ol remain in the form of an oil. $^1$H-NMR (200 MHz, CDCl$_3$): δ=1.16 (s, 3H), 1.3–1.8 (m, 8H), 1.9 (d, 1H), 2.45 (dd, 1H), 3.06 (d, 1H), 3.42 (d, 1H), 7.1–7.27 (m, 4H) ppm.

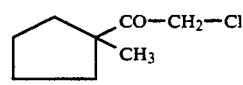
(VII-1)

A mixture of 1040 g (4.4 mol) of 2-chloro-1-(1-methyl-cyclopent-1-yl)-1-phenoxy-ethene, 4 liters of formic acid and 400 ml of water is heated at 80° C. with stirring for 1 hour. After cooling to room temperature, the reaction mixture is diluted with methylene chloride and then extracted by shaking twice with water and three times with dilute aqueous sodium hydroxide solution. The organic phase is concentrated, after drying over sodium sulphate, by stripping off the solvent under reduced pressure. The residue which remains is subjected to a fractional vacuum distillation.

604 g (85.5% of theory) of 1-chloroacetyl-1-methyl-cyclopentane are obtained in this manner in the form of a liquid of boiling point 85°–95° C./10 mbar.

NMR (CDCl$_3$); δ=1.3 (s, 3H), 1.4–2.2 (m, 8H), 4.4 (s,

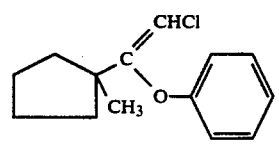
(XI-1)

A mixture of 1074 g (6 mol) of 1-(2,2-dichloroethenyl)-1-methyl-cyclopentane, 835 g (7.2 mol) of phenoxide, 828 g (6 mol) of anhydrous potassium carbonate and 6 liters of N-methylpyrrolidone is heated at 200° C. for 5 hours. After cooling the reaction mixture to room temperature, it is first diluted with methylene chloride and then extracted by shaking once with water and several times with dilute aqueous sodium hydroxide solution. The organic phase is dried over sodium sulphate and concentrated by stripping off the solvent under reduced pressure. 2.5 kg of a residue remain which is fractionally distilled through a column. By collecting the fraction which boils between 100° C. and 120° C. at 0.1 mbar, 1043 g of a product which consists to 83.1% of 2-chloro-1-(1-methyl-cyclopent-1-yl)-1-phenoxy-ethene are obtained according to the gas chromatogram. The yield is then calculated to be 73.5%.

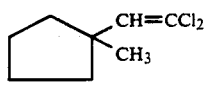 (X-1)

150 g (1.13 mol) of powdered aluminum chloride are added in portions at 0° C. with stirring and further cooling to a mixture of 575 g (6.85 mol) of methylcyclopentane, 634 g (6.85 mol) of tert.-butyl chloride and 1.99 kg (20.55 mol) of 1,1-dichloroethene. After addition is complete, the mixture is first stirred for 2 hours and 50 g of aluminum chloride are then added once more. The reaction mixture is stirred at 0° C. to 10° C. for 2 hours and then poured onto ice and dilute hydrochloric acid. The mixture is extracted several times using methylene chloride, and the combined organic phases are dried over sodium sulphate and concentrated by stripping off the solvent under reduced pressure. 1.4 kg of a product remain which is subjected to a fractional distillation under reduced pressure. In this case two fractions are collected, namely a) 434 g of a product which boils between 27° C. and 66° C. at 30 mbar, and b) 622 g of a product which boils between 90° C. and 130° C. at 25 mbar.

The second fraction consists to 85% of 1-(2,2-dichloroethenyl)-1-methyl-cyclopentane according to the gas chromatogram. This product is used for the further reactions.

The substances according to the invention shown in Table 2 below can be prepared by the methods previously mentioned.

TABLE 2

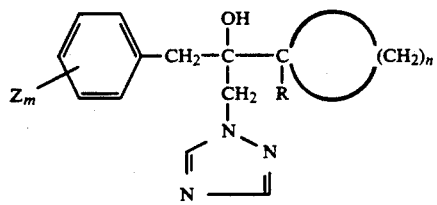 (I)

| Ex. No. | Compound No. | $Z_m$ | R | n | m.p. (°C.) |
|---|---|---|---|---|---|
| 3 | I-3 | 2,4-Cl$_2$ | CH$_3$ | 5 | 154 |
| 4 | I-4 | 4-Cl | CH$_3$ | 5 | 104 |
| 5 | I-5 | 4-F | CH$_3$ | 4 | 136 |
| 6 | I-6 | 2-F | CH$_3$ | 4 | 106 |
| 7 | I-7 | 2-Cl | C$_2$H$_5$ | 4 | NMR spectrum* |
| 8 | I-8 | 4-Cl | CH$_3$ | 5 | 122 (× saccharin) |
| 9 | I-9 | 2-Cl | CH$_3$ | 5 | 95 (× saccharin) |
| 10 | I-10 | 4-F | CH$_3$ | 4 | 122 (× saccharin) |
| 11 | I-11 | 2,4-Cl$_2$ | CH$_3$ | 5 | 144 (× saccharin) |

TABLE 2-continued

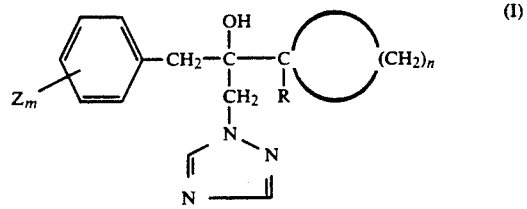 (I)

| Ex. No. | Compound No. | $Z_m$ | R | n | m.p. (°C.) |
|---|---|---|---|---|---|
| 12 | I-12 | 2-F | CH$_3$ | 4 | 143 (× saccharin) |

*NMR spectrum of compound No. (I-7)

$^1$H-NMR (200 MHz, CDCl$_3$): δ=1.03 (t, 3H), 1.35–2.05 (m, 10H), 2.95 (d, 1H), 3.42 (d, 1H), 4.20 (d, 1H), 4.21 (s, 1H), 4.35 (d, 1H), 7.05–7.42 (m, 4H), 7.63 (s, 1H), 7.72 (s, 1H) ppm.

Example A

Pyricularia test (rice)/protective
Solvent: 12.5 parts by weight of acetone
Emulsifier: 0.3 parts by weight of alkylaryl polyglycol ether To produce a suitable preparation of active with the stated amount of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, substances (I-1) and (I-2) according to the invention show a very good activity.

Example B

Pellicularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for activity, young rice plants in the 3 to 4 leaf stage are sprayed until dripping wet. The plants remain in a greenhouse until they have dried off. The plants are then inoculated with Pellicularia sasakii and are placed at 25° C. and 100% relative atmospheric humidity.

The evaluation of the disease infestation is carried out 5 to 8 days after the inoculation.

In this test, substances (I-1) and (I-2) according to the invention show a very good activity.

Example C

Botrytis test (paprika)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of Botrytis cinerea.

The plants then remain in an incubation cabinet for 4 days until evaluation at 20° C. and 100% relative atmospheric humidity.

In this test, substances (I-1) and (I-2) according to the invention show a very good activity.

Example D

Venturia test (apple)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, substances (I-1) and (I-2) according to the invention show a very good activity.

Example E

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, substances (I-1) and (I-2) according to the invention show a very good activity. cl Example F Botrytis test (beans)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet After the spray coating has dried on, 2 small pieces of agar covered with Bolrylis cinerea are placed on each leaf. The inoculated plants are placed in a darkened humidity chamber at 20° C. 3 days after the inoculation, the size of the infected spots on the leaves is evaluated.

In this test, substances (I-1) and (I-2) according to the invention show a very good activity.

Example G

Ventura test (apple)/curative
Solvent: 4.7 parts by weight of acetone
Emulsifier 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous conidia suspension of the apple scab causative organism (Venturia inaequalis). The plants remain in an incubation cabin at 20° C. and 100% relative atmospheric humidity for 1 day and are then placed in a greenhouse. After a given number of hours, the plants are sprayed with the preparation of active compound until dripping wet.

Evaluation is carried out 12 days after the inoculation.

In this test, substances (I-1) and (I-2) according to the invention show a very good activity.

It will be understood that the specification and examples are illustrative but not limitative of the present invention and that other embodiments within the spirit and scope of the invention will suggest themselves to those skilled in the art.

We claim:

1. A 1-(4-chlorophenyl)-2-(1-methyl-cyclohex-1-yl)-3-(1,2,4-triazol-1-yl propan-2-ol of the formula

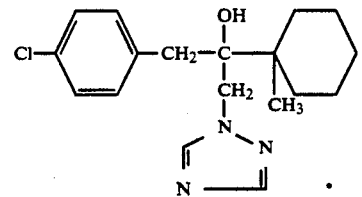

2. A fungicidal composition comprising a fungicidally effective amount of a compound or addition product thereof according to claim 1 and a diluent.

3. A method of combating fungi which comprises applying to such fungi or to a locus from which it is desired to exclude such fungi a fungicidally effective amount of a compound or addition product thereof according to claim 1.

* * * * *